United States Patent
Somekawa

(10) Patent No.: US 12,245,742 B2
(45) Date of Patent: Mar. 11, 2025

(54) ENDOSCOPE

(71) Applicant: HOYA CORPORATION, Tokyo (JP)

(72) Inventor: Kensei Somekawa, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 513 days.

(21) Appl. No.: 16/484,257

(22) PCT Filed: Jan. 24, 2018

(86) PCT No.: PCT/JP2018/002061
§ 371 (c)(1),
(2) Date: Aug. 7, 2019

(87) PCT Pub. No.: WO2018/179737
PCT Pub. Date: Oct. 4, 2018

(65) Prior Publication Data
US 2019/0374091 A1 Dec. 12, 2019

(30) Foreign Application Priority Data
Mar. 31, 2017 (JP) .................. 2017-072397

(51) Int. Cl.
*A61B 1/00* (2006.01)
*A61B 1/005* (2006.01)

(52) U.S. Cl.
CPC ........ *A61B 1/00078* (2013.01); *A61B 1/0055* (2013.01); *A61B 1/0016* (2013.01)

(58) Field of Classification Search
CPC .. A61B 1/0016; A61B 1/0055; A61B 1/00078
See application file for complete search history.

(56) References Cited

U.S. PATENT DOCUMENTS

| | | | | |
|---|---|---|---|---|
| 5,482,029 | A | * | 1/1996 | Sekiguchi ............ A61B 1/0005 600/109 |
| 5,876,325 | A | * | 3/1999 | Mizuno ................ A61B 34/37 600/117 |
| 6,485,411 | B1 | | 11/2002 | Konstorum et al. |
| 2004/0193013 | A1 | * | 9/2004 | Iwasaka ................ B32B 27/32 600/140 |

(Continued)

FOREIGN PATENT DOCUMENTS

| CN | 105852780 A | | 8/2016 | |
|---|---|---|---|---|
| JP | S628728 | * | 1/1987 | ............... A61B 1/00 |

(Continued)

OTHER PUBLICATIONS

English Translation of JP4396789 (Year: 2010).*

(Continued)

*Primary Examiner* — Aaron B Fairchild
*Assistant Examiner* — Megan Elizabeth Monahan
(74) *Attorney, Agent, or Firm* — GREENBLUM & BERNSTEIN P.L.C.

(57) ABSTRACT

An endoscope is provided which has a high insertability, that is, is easy to insert. The endoscope includes an insertion unit having a first area in which an attenuation rate of a repulsive force generated when bent is a positive value of 30% or lower. More preferably, the attenuation rate of the first area is 10% or higher and 30% or lower. The first area is in a range of 200 mm to 800 mm from a distal end side of the insertion unit.

14 Claims, 8 Drawing Sheets

(56) References Cited

U.S. PATENT DOCUMENTS

| | | | |
|---|---|---|---|
| 2010/0217184 A1* | 8/2010 | Koblish | A61M 25/0141 |
| | | | 604/95.01 |
| 2012/0053417 A1 | 3/2012 | Yamakawa et al. | |
| 2016/0227982 A1 | 8/2016 | Takahashi et al. | |
| 2016/0353980 A1* | 12/2016 | Takahashi | A61B 1/00078 |

FOREIGN PATENT DOCUMENTS

| | | | | |
|---|---|---|---|---|
| JP | S628728 A * | 1/1987 | | A61B 1/00 |
| JP | H01-212532 A | 8/1989 | | |
| JP | 4396789 * | 1/2010 | | A61M 25/00 |
| JP | 4396789 B2 * | 1/2010 | | A61M 25/00 |
| JP | 2012-050557 A | 3/2012 | | |

OTHER PUBLICATIONS

U.S. Appl. No. 16/484,270 to Yuki Tajima et al., which was filed on Aug. 7, 2019.

U.S. Appl. No. 16/484,173 to Yuki Tajima et al., which was filed on Aug. 7, 2019.

International Search Report issued in International Patent Application No. PCT/JP2018/002061, dated Apr. 3, 2018.

Office Action issued in Chinese Counterpart Patent Appl. No. 201880011025.8, dated Apr. 22, 2021, together with a English language translation thereof.

\* cited by examiner

ENDOSCOPE

TECHNICAL FIELD

The present invention relates to an endoscope.

BACKGROUND ART

A hardness adjuster described in Patent Literature 1 is proposed in order to enhance insertability of an endoscope, that is, the ease of insertion.

CITATION LIST

Patent Literature

Patent Literature 1: JP 2012-050557 A

SUMMARY OF INVENTION

Technical Problem

However, there is a possibility that the ease of insertion is not sufficient only with the hardness adjuster described in Patent Literature 1.

Therefore, an object is to provide an endoscope with a high insertability, in one aspect.

Solution to Problem

An endoscope includes an insertion unit having a first area in which an attenuation rate of a repulsive force generated when bent is a positive value of 30% or lower.

Advantageous Effects of Invention

In one aspect, it is possible to provide the endoscope with the high insertability.

DESCRIPTION OF EMBODIMENTS

First Embodiment

Figure 1:
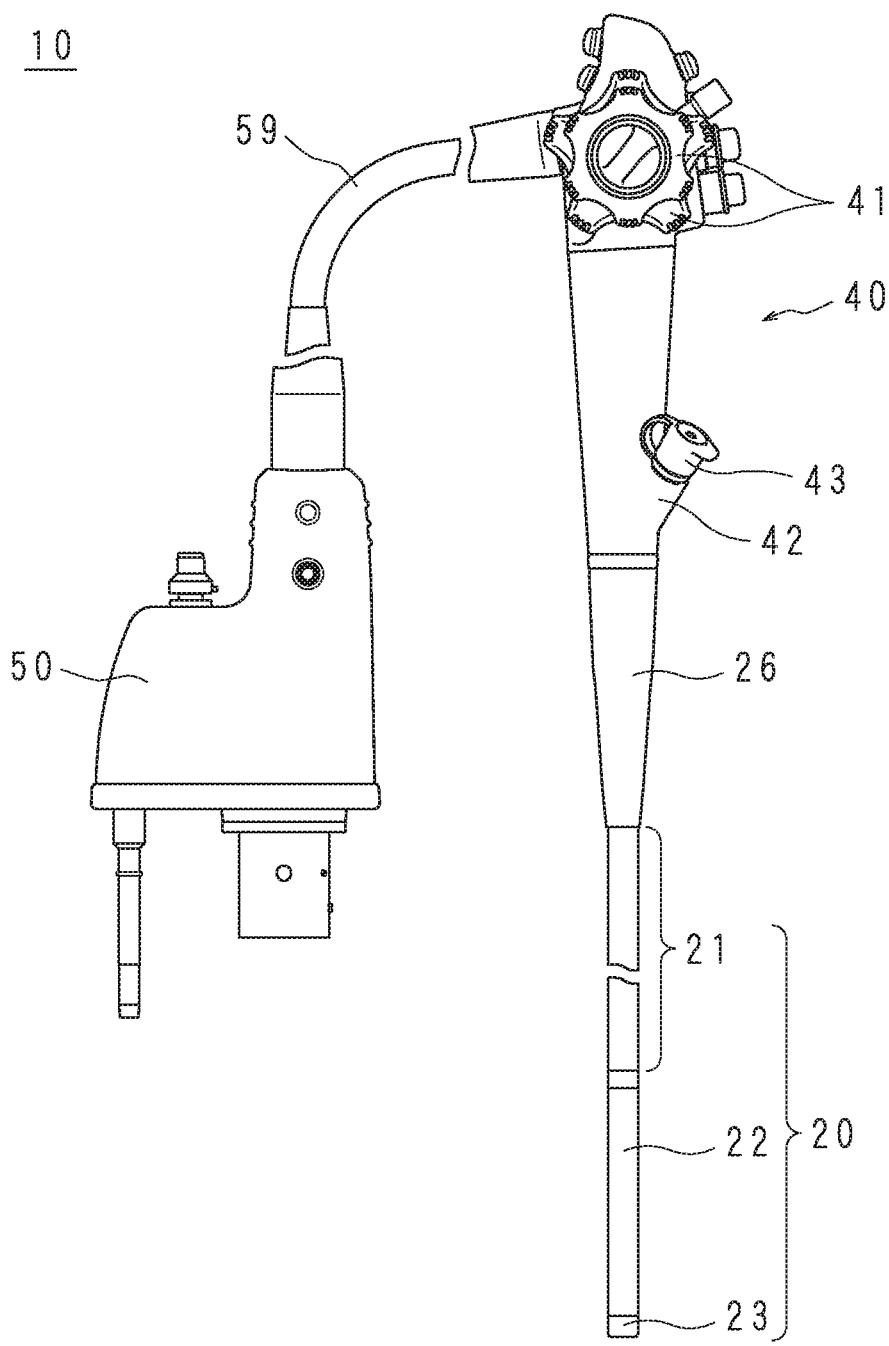
FIG. 1 is an exterior view of an endoscope.

FIG. 1 is an exterior view of an endoscope 10. The endoscope 10 of the present embodiment is a flexible scope for a lower gastrointestinal tract. The endoscope 10 includes an insertion unit 20, an operation unit 40, a universal cord 59, and a connector unit 50. The operation unit 40 includes a bending knob 41 and a channel inlet 42. A forceps plug 43 having an insertion port to insert a treatment tool or the like is fixed to the channel inlet 42.

The insertion unit 20 is long and has one end connected to the operation unit 40 via a bend preventing portion 26. The insertion unit 20 includes a soft portion 21, a bending portion 22, and a distal end portion 23 in the order from the operation unit 40 side. The soft portion 21 is soft. A surface of the soft portion 21 is a tube-shaped flexible tube 30 (see FIG. 3). The bending portion 22 is bent according to an operation of the bending knob 41.

In the following description, a longitudinal direction of the insertion unit 20 is referred to as an insertion direction. Similarly, a side close to the operation unit 40 along the insertion direction is referred to as an operation unit side, and a side far from the operation unit 40 is referred to as a distal end side.

The universal cord 59 is long, and has a first end connected to the operation unit. 40 and a second end connected to the connector unit. 50. The universal cord 59 is soft. The connector unit 50 is connected to a video processor (not illustrated), a light source device, a display device, an air and water supply device, and the like.

Figure 2:
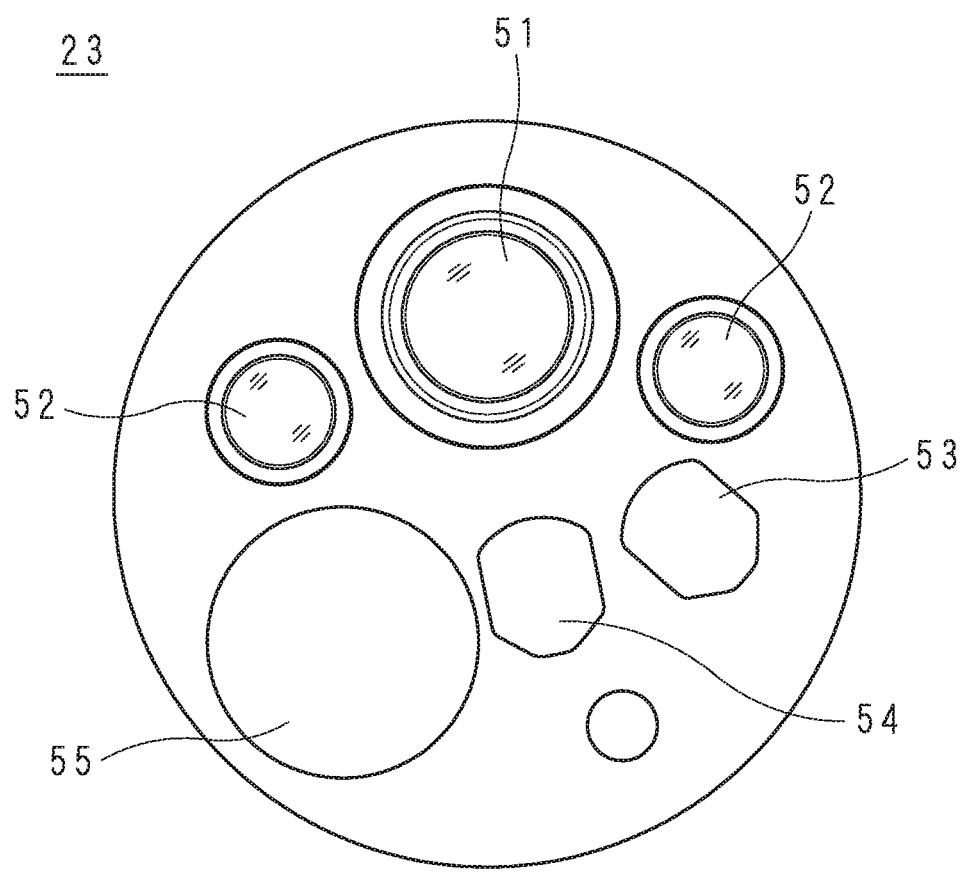
FIG. 2 is an external view of an end surface of a distal end portion.

FIG. 2 is an external view of as end surface of the distal end portion 23. An observation window 51, two illumination windows 52, an air supply nozzle 53, a water supply nozzle 54, a channel outlet 55, and the like are provided on the end surface of the distal end portion 23.

The end surface of the distal end portion 23 has a substantially circular shape. The observation window 51 is provided above a center of the end surface in FIG. 2. The illumination windows 52 are provided on the left and right of the observation window 51. The air supply nozzle 53 and the water supply nozzle 54 are provided with outlets facing the observation window 51 at the lower right of the observation window 51. The channel outlet 55 is provided at the lower left of the observation window 51.

The description on the configuration of the endoscope 10 will be continued using FIGS. 1 and 2. A fiber bundle, a cable bundle, an air supply tube, a water supply tube, and the like are inserted inside the connector unit 50, the universal cord 59, the operation unit 40, and the insertion unit 20. Illumination light emitted from a light source device is emitted from the illumination window 52 through the fiber bundle. A range illuminated by the illumination light is captured by an imaging element (not illustrated) via the observation window 51. A video signal is transmitted from the imaging element to the video processor via the cable bundle.

Air supplied from the air supply/water supply device is discharged from the air supply nozzle 53 toward the observation window 51 via the air supply tube. Similarly, water supplied from the air and water supply device is discharged from the water supply nozzle 54 toward the observation window 51 via the water supply tube. The air supply nozzle 53 and the water supply nozzle 54 are used, for example, to clean the observation window 51 during an endoscopy.

The channel inlet 42 and the channel outlet 55 are connected by a tube-shaped channel passing through each inside of the soft portion 21 and the bending portion 22. As a treatment tool (not illustrated) is inserted from the channel inlet 42, a distal end of the treatment tool can be caused to protrude from the channel outlet 55 to perform a procedure such as removal of a large intestine polyp.

Figure 3:
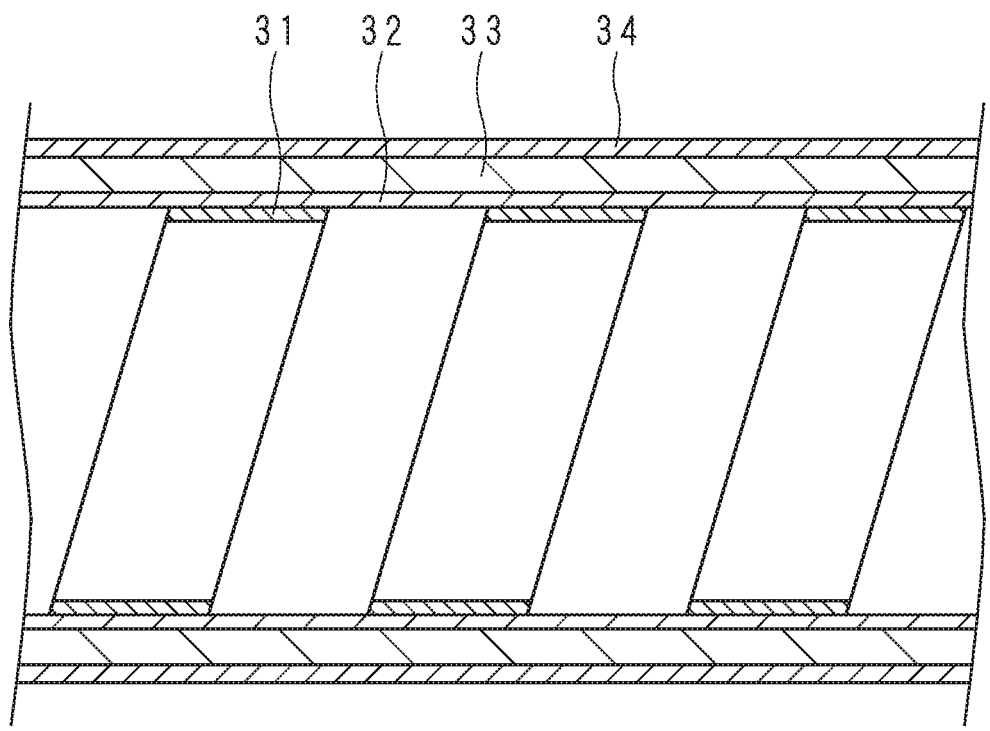
FIG. 3 is a cross-sectional view of a flexible tube.

FIG. 3 is a cross-sectional view of the flexible tube 30. As described above, the flexible tube 30 is an exterior member of the soft portion 21. FIG. 3 illustrates a cross section of the flexible tube 30 cut along the insertion direction.

The flexible tube 30 has a configuration in which an outer side of a spiral tube 31 obtained by spirally winding strip-shaped metal is sequentially covered with a reticular tube 32, a hull 33, and a top coat 34. The spiral tube 31 protects internal components, such as the fiber bundle, the cable bundle, and various tubes inserted inside, so as not to be crushed when the soft portion 21 is bent.

The reticular tube 32 is formed by braiding a thin wire material. The thin wire material is, for example, a stainless steel wire or a copper alloy wire. The thin wire material may be non-metal.

The hull 33 is a layer of resin molded on the outer side of the reticular tube 32. Examples of a material of the hull 33 includes polyolefin such as an ethylene-vinyl acetate copolymer, fluororesin such as polytetrafluoroethylene and an ethylene-tetrafluoroethylene copolymer, a polyester elastomer, a polyolefin elastomer, a fluorine-based elastomer, a polyurethane elastomer, a polyamide elastomer, silicone rubber, fluororubber, and the like. The hull 33 may be a laminate of a plurality of resin layers. A plurality of resin materials may be mixed to form the hull 33.

The top coat 34 is, for example, a urethane resin or a fluorine resin. The top coat 34 protects the hull 33 from a chemical solution or the like which is used to clean and disinfect the endoscope 10.

A user of the endoscope 10 according to the present embodiment inserts the insertion unit 20 from the anus of a person to be examined. The user guides the distal end of the insertion unit 20 to a target site while observing a captured image through the observation window 51. At a part where the large intestine is strongly bent, the user operates the bending knob 41 to bend the bending portion 22 and performs an operation such as twisting the insertion unit 20 so as to advance the distal end portion 23 toward the cecum. The insertion unit 20 having entered the inside of the large intestine is pushed by a wall of the large intestine and is passively bent.

The insertion unit 20 bent by an external force generates a repulsive force due to the rigidity of the flexible tube 30 and the internal components inserted into the flexible tube 30. The repulsive force decreases as time elapses with a peak immediately after bending.

Figure 4:
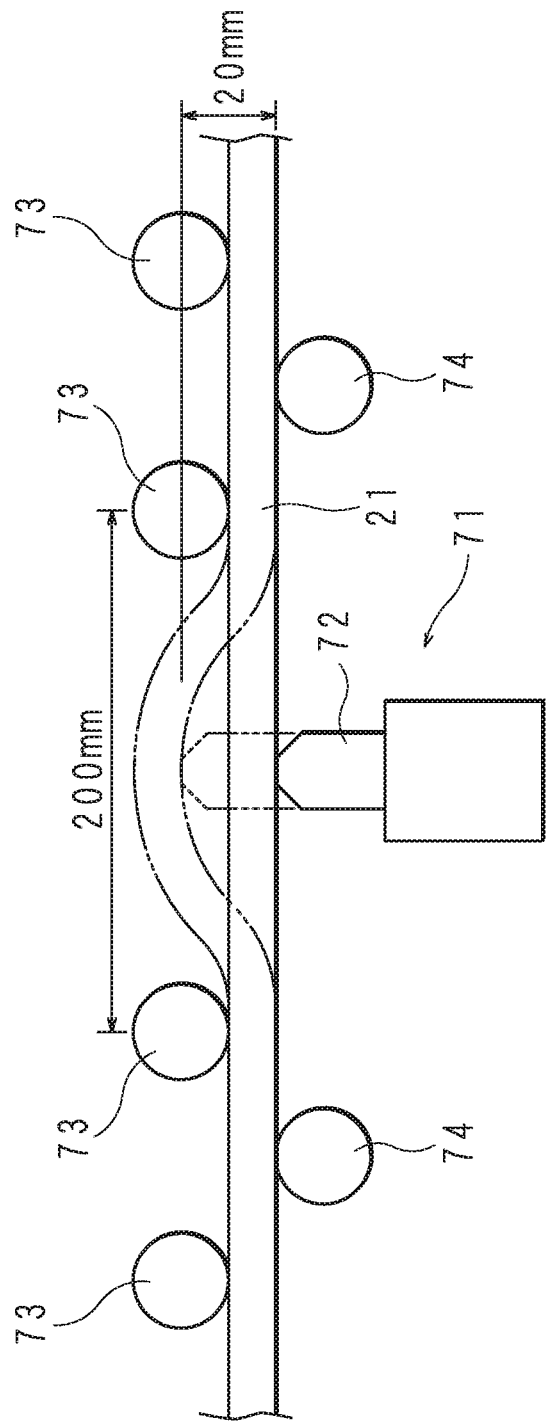
FIG. 4 is an explanatory view for describing a method of measuring a repulsive force.

FIG. 4 is an explanatory view for describing a method of measuring the repulsive force. FIG. 4 is a top view of a measurement device 70 for the repulsive force. The measurement device 70 includes four pressing columns 73, two auxiliary columns 74, and a load measuring instrument 71. The load measuring instrument 71 is a measuring instrument that measures a load applied to a probe 72 protruding from one side.

The pressing column 73 and the auxiliary column 74 are cylindrical and fixed vertically to a horizontally installed test stand. The four pressing columns 73 are arranged in a straight line, and a distance between central axes of two central pressing columns is 200 mm. The two auxiliary columns 74 are arranged in a straight line parallel to the arrangement of the pressing columns 73.

The soft portion 21 is arranged straight and horizontally between the pressing column 73 and the auxiliary column 74. The probe 72 abuts perpendicularly against a central portion between the central two pressing columns 73 in the longitudinal direction of the soft portion 21 from the opposite side of the pressing column 73.

The soft portion 21 is pushed by 20 mm by the probe 72. As illustrated by a two-dot chain line in FIG. 4, the soft portion 21 is turned into a three-point bending state of bending at three points of the central two pressing columns 73 and the probe 72. Since the soft portion 21 is held by the outer pressing columns 73 and the auxiliary column 74 in a part outside the three-point bending state, it is possible to perform measurement with a high reproducibility.

As described above, the configuration illustrated in FIG. 4 illustrates a three-point bending tester with the spacing of 200 millimeters. The load measuring instrument 71 can measure a repulsive force of the insertion unit 20, which is an object to be measured, pushing back the probe 72 when a central point in the three-point bending tester with the spacing of 200 millimeters is pushed by 20 mm in a direction perpendicular to the longitudinal direction of the insertion unit 20.

Figure 5:
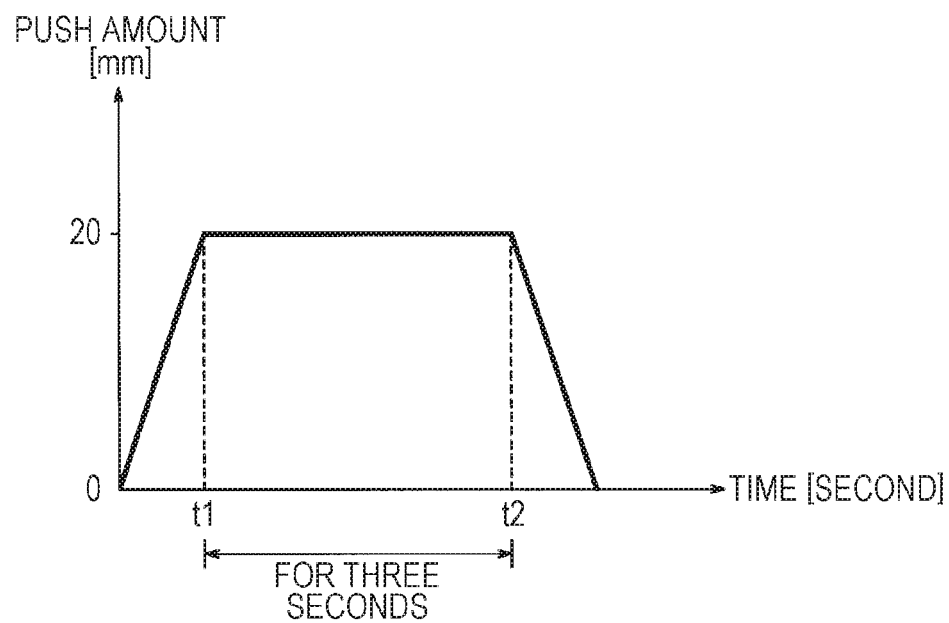
FIG. 5 is a graph for describing the method of measuring the repulsive force.

FIG. 5 is a graph for describing the method of measuring the repulsive force. The horizontal axis of FIG. 5 represents time, and the unit is a second. The vertical axis in FIG. 5 represents a push amount of the probe 72, and the unit is a millimeter. The push amount is measured using, as a reference, a state where the two pressing columns 73 and the probe 72 are in contact with the soft portion 21 arranged straight and horizontally as indicated by a solid line in FIG. 4.

The push of the probe 72 is started from a time zero. At a time t1, the probe 72 is set to a state of being pushed by 20 mm as indicated by a two-dot chain line in FIG. 4. Such a state is held for three seconds until a time t2. After the time t2, the probe 72 is returned to its original position.

Figure 6:
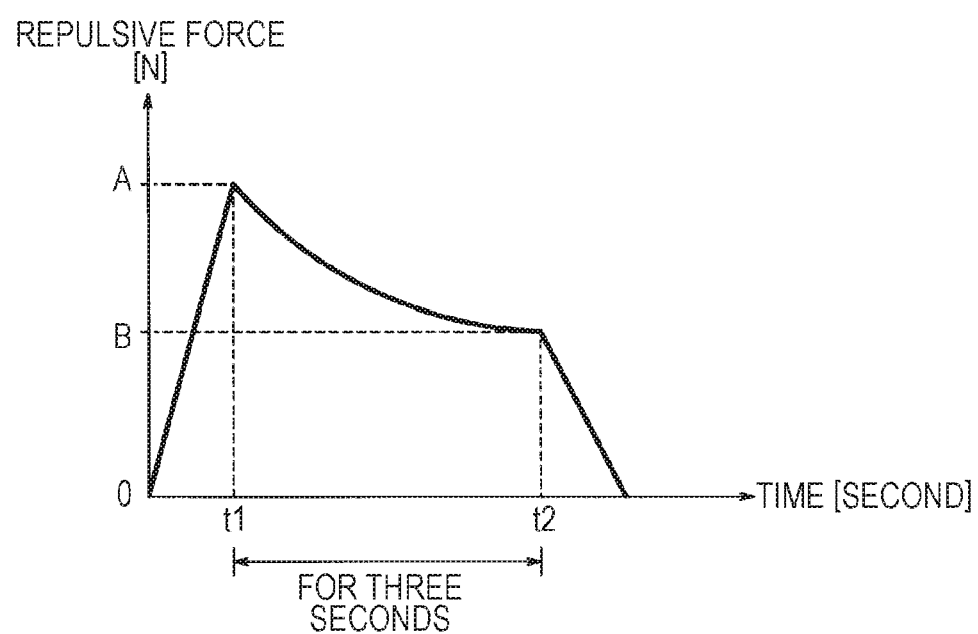
FIG. 6 is a graph for describing the method of measuring the repulsive force.

FIG. 6 is a graph for describing the method of measuring the repulsive force. The horizontal axis of FIG. 6 represents time, and the unit is a second. Times t1 and t2 on the horizontal axis in FIG. 6 coincide with the times t1 and t2 on the horizontal axis in FIG. 5. The vertical axis in FIG. 6 represents a repulsive force of the soft portion 21 measured by the load measuring instrument 71, and the unit is a Newton.

As illustrated in FIG. 6, the repulsive force has a maximum value A at the time t1. The repulsive force rapidly decreases from the time t1 and settles to a stable value B by the time t2. After the time t2, when the probe 72 is returned to the original position, the repulsive force returns to zero.

An attenuation rate C of the repulsive force at a position where the probe 72 abuts is defined by Formula (1).

[Formula 1]

$$C = \frac{A - B}{A} \times 100 \qquad (1)$$

A is a maximum value of a repulsive force.
B is a repulsive force after three seconds from push.
C is an attenuation rate (percentage) of a repulsive force at a position of abutment on a probe 72.

In FIG. 4, the repulsive force at each position of the soft portion 21 can be measured by causing the soft portion 21 to slide to the left and right and measuring the repulsive force. Incidentally, the bending portion 22 and the bend preventing portion 26 do not abut against the pressing column 73 in the measurement. Therefore, the attenuation rate C of the repulsive force is not measured in a range of just over 100 mm from each of both ends of the soft portion 21.

Figure 7:
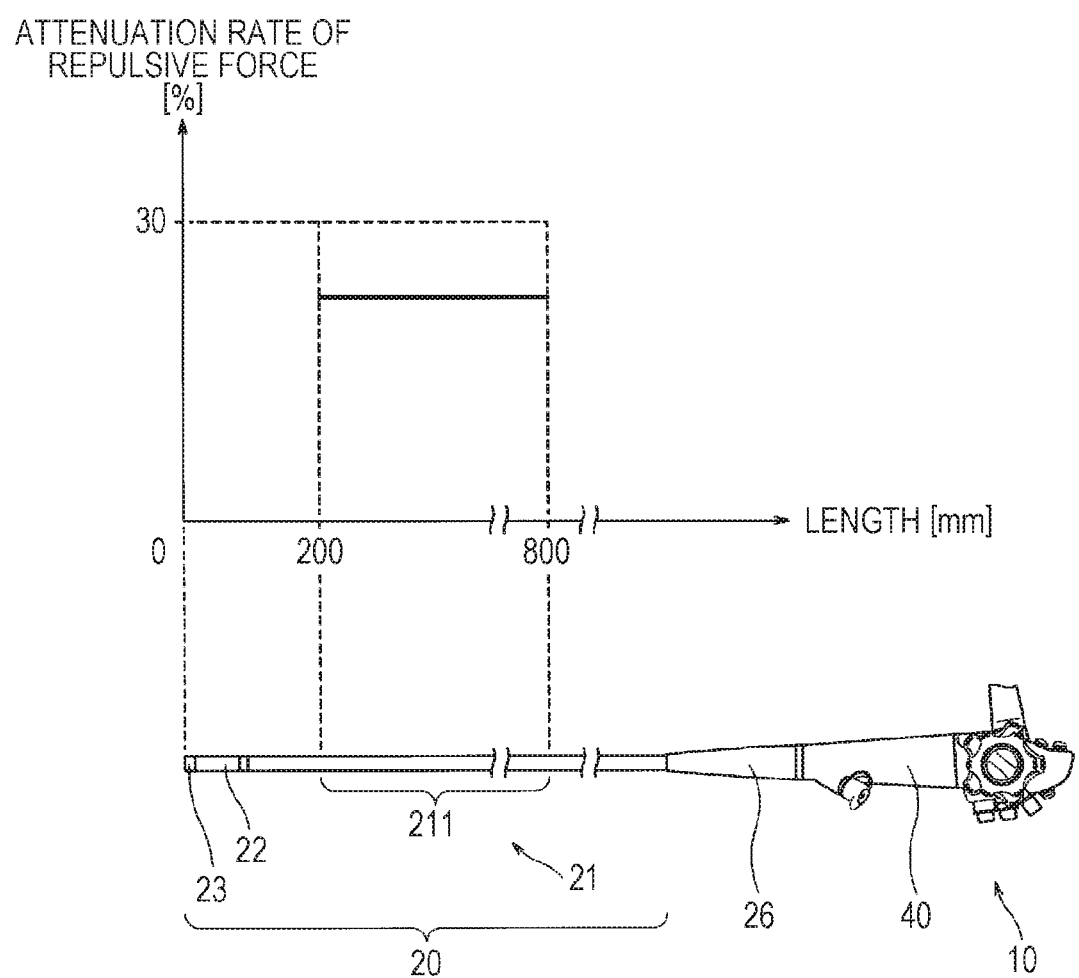
FIG. 7 is an explanatory view for describing an example of an attenuation rate of the repulsive force.

FIG. 7 is an explanatory view for describing an example of the attenuation rate of the repulsive force. An appearance of the endoscope 10 is illustrated on the lower side of FIG. 7. A graph of the repulsive force is illustrated on the upper side of FIG. 7. The horizontal axis of the graph represents a length from the distal end of the insertion unit 20, and the unit is a millimeter position on the horizontal axis corresponds to the appearance of the endoscope 10 illustrated on the lower side of FIG. 7.

The vertical axis of the graph represents the attenuation rate of the repulsive force of the soft portion 21 described using FIGS. 4 to 6, and the unit is a percentage. In the present embodiment, the repulsive force and the attenuation rate thereof are not measured for a part whose horizontal axis is less than 200 mm. In the example illustrated in FIG. 7, the attenuation rate of the repulsive force of a first area 211 in a range of 200 millimeters or more and 800 millimeters or less on the horizontal axis is a substantially constant value of 30% or lower.

The attenuation rate of the repulsive force of a part in a range where the horizontal axis is longer than 600 mm is arbitrary, and may be 30% or lower or higher than 30%. Further, the attenuation rate of the repulsive force of this part may be uniform or may be changed along the insertion direction.

Since the soft portion 21 in which the attenuation rate of the repulsive force is 30% or lower is provided in the first area 211 which is an area close to the distal end side as illustrated in FIG. 7, the insertion unit 20 is hardly lose against a repulsive force of the large intestine. Furthermore, the soft portion 21 in which the attenuation rate of the repulsive force is 30% or lower is hardly bent or wrinkled along a shape of the large intestine, and is also hardly deflected. With these effects, it is possible to provide the endoscope 10 with a high insertability in which the distal end portion 23 proceeds inside the large intestine as intended by the user.

The attenuation rate of the repulsive force in the first area 211 is preferably 10% or higher and 30% or lower, and more preferably, is 10% or higher and 25% or lower.

A specific example of a method of controlling the attenuation rate of the repulsive force of the first area 211 to 30% or lower will be described hereinafter. The attenuation rate of the repulsive force is defined by a configuration of the flexible tube 30 and configurations of the internal components inserted into the flexible tube 30. The configurations of the internal component is mainly defined based on the specification of the endoscope 10. Hereinafter, an example of an experimental result obtained by adjusting the configuration of the flexible tube 30 without changing the configurations of the internal components will be illustrated.

[Experimental Result-1]

As described above, various resins can be used for the hull 33. It is possible to adjust residual strain that occurs after once stretching the resin by selecting the resin to be used.

Here, a method of measuring residual strain in the present embodiment will be described. For the measurement, a dumbbell-shaped No. 3 test piece defined in JIS (Japan Industrial Standard) K6251 "Rubber, vulcanized or thermoplastics-Determination of tensile stress-strain properties" is used. It is possible to create a test piece by molding a resin material to be used for the hull 33 into a thin plate having a predetermined thickness and then punching out the molded resin material with a predetermined punching blade.

Since the method of measuring residual strain is not defined in the above-described JIS standard, an overview of the measurement method will be described hereinafter. Incidentally, it is possible to use the same precision universal tester and grippers as those in the above-described JIS standard for the measurement.

The test piece is mounted in the precision universal tester. A distance between the grippers of the precision universal tester is set to 50 mm. The grippers are pulled apart at 20 mm per second to stretch the test piece by 5 mm. The test piece is held for 180 seconds in the stretched state. Thereafter, the grippers are returned to their original positions at 20 mm per second, and the test piece is removed from the grippers.

A stretch amount L2 of the removed test piece is measured. Residual strain is calculated by Formula (2).

[Formula 2]

$$Ts = \frac{L2}{L1} \times 100 \qquad (2)$$

Ts is residual strain (percentage).
L1 is displacement when being stretched, and is 5 millimeters in the present embodiment.
2 is a stretch amount of a removed test piece.

The four endoscopes 10 were manufactured using four types of resin materials whose residual strain was measured according to the above procedure as the hull 33. Incidentally, the four endoscopes 10 have the same configurations except for the material of the hull 33. The attenuation rate of the repulsive force of the first area 211 was measured by the method described using FIGS. 4 to 6.

The insertion unit 20 of the endoscope 10 was inserted into a large intestine model simulating a shape of the large intestine, and the insertion property was evaluated in three stages. "3" indicates that the insertion unit 20 can be smoothly inserted into the large intestine model. "2" indicates that the insertion unit 20 is sometimes deflected and hardly inserted when passing over a bending portion of the large intestine model. "1" indicates that the insertion unit 20 is easily deflected when passing over the bending portion of the large intestine model, and it is not possible to insert the distal end portion 23 up to the back of the large intestine model. Table 1 shows experimental results.

TABLE 1

| Number | Residual Strain Ts [%] | Attenuation Rate of Repulsive Force [%] | Insertability to Large Intestine Model |
|---|---|---|---|
| No. 1 | 18 | 10-20 | 3 |
| No. 2 | 22 | 20-25 | 2 |
| No. 3 | 27 | 25-30 | 2 |
| No. 4 | 29 | 30-35 | 2 |

As illustrated in Table 1, it is possible to realize the insertion unit 20 with the low attenuation rate of the repulsive force by using the resin with small residual strain for the hull 33. It is possible to realize the insertion unit 20 with the high attenuation rate of the repulsive force by using the resin with large residual strain for the hull 33.

As shown in Table 1, the endoscope 10 of No. 1 provided with the insertion unit 20 in which the attenuation rate of the repulsive force is 10 to 20% has a high insertability into the large intestine model.

[Experimental Result-2]

The attenuation rate of the repulsive force can also be changed depending on a thickness of the top coat 34. The thickness of the top coat 34 can be measured by measuring a thickness of the flexible tube 30 before and after coating with the top coat 34 using a laser profile measuring instrument. Incidentally, the measurement is performed in two directions orthogonal to each other, and an average value is obtained.

Four endoscopes 10 different in thickness of the top coat 34 were manufactured. The four endoscopes 10 have the same configurations except for the thickness of the top coat 34. Similar to Experimental Result-1, the attenuation rate of the repulsive force was measured, and the insertability into the large intestine model was evaluated in three stages. Table 2 shows experimental results.

TABLE 2

| Number | Thickness of Top Coat [μm] | Attenuation Rate of Repulsive Force [%] | Insertability to Large Intestine Model |
|---|---|---|---|
| No. 5 | 10-30 | 10-20 | 3 |
| No. 6 | 30-60 | 20-25 | 2 |
| No. 7 | 60-120 | 25-30 | 2 |
| No. 8 | 120-250 | 30-35 | 1 |

As shown in Table 2, it is possible to realize the insertion unit 20 having the low attenuation rate of the repulsive force by thinning the top coat 34. It is possible to realize the insertion unit 20 having the high attenuation rate of the repulsive force by thickening the top coat 34.

As shown in Table 2, the endoscope 10 of No. 5 provided with the insertion unit 20 in which the attenuation rate of the repulsive force is 10 to 20% has a high insertability into the large intestine model. The endoscope 10 of No. 8 provided with the insertion unit 20 in which the attenuation rate of the repulsive force is 30 to 35% has a low insertability into the large intestine model.

The attenuation rate of the repulsive force of the insertion unit 20 can be appropriately adjusted by defining the configurations of the internal components based on the specification of the endoscope 10, and then, defining the resin to be used for the hull 33 and the thickness of the top coat 34.

The attenuation rate of the repulsive force of the insertion unit 20 may be adjusted by adjusting a material, a width and a thickness of a wire, a pitch of the spiral, and the like of the spiral tube 31. The attenuation rate of the repulsive force of the insertion unit 20 may be adjusted by adjusting a material, a thickness of a wire, a method of knitting, and the like of the reticular tube 32.

Although the endoscope 10 for the lower gastrointestinal tract has been described as an example in the present embodiment, the endoscope 10 may be directed to an upper gastrointestinal tract or a respiratory organ.

Although the so-called direct-view endoscope 10 in which the insertion direction coincides with a field-of-view direction has been described as an example in the present embodiment, the endoscope 10 may be of a side-view type, as oblique-view type, or the like is which the insertion direction is different from the field-of-view direction.

The attenuation rate of the repulsive force can be adjusted depending on the thickness of the hull 33, the thickness and knitting method of the wire forming the reticular tube 32, materials of tubes of the internal components, and the like.

According to the present embodiment, it is possible to provide the endoscope 10 with the high insertability.

Second Embodiment

The present embodiment relates to the endoscope 10 including the first area 211 and a second area 212 which is adjacent to a distal end side of the first area 211 and has an attenuation rate of a repulsive force higher than that of the first area 211. Descriptions regarding common parts with the first embodiment will be omitted.

Figure 8:
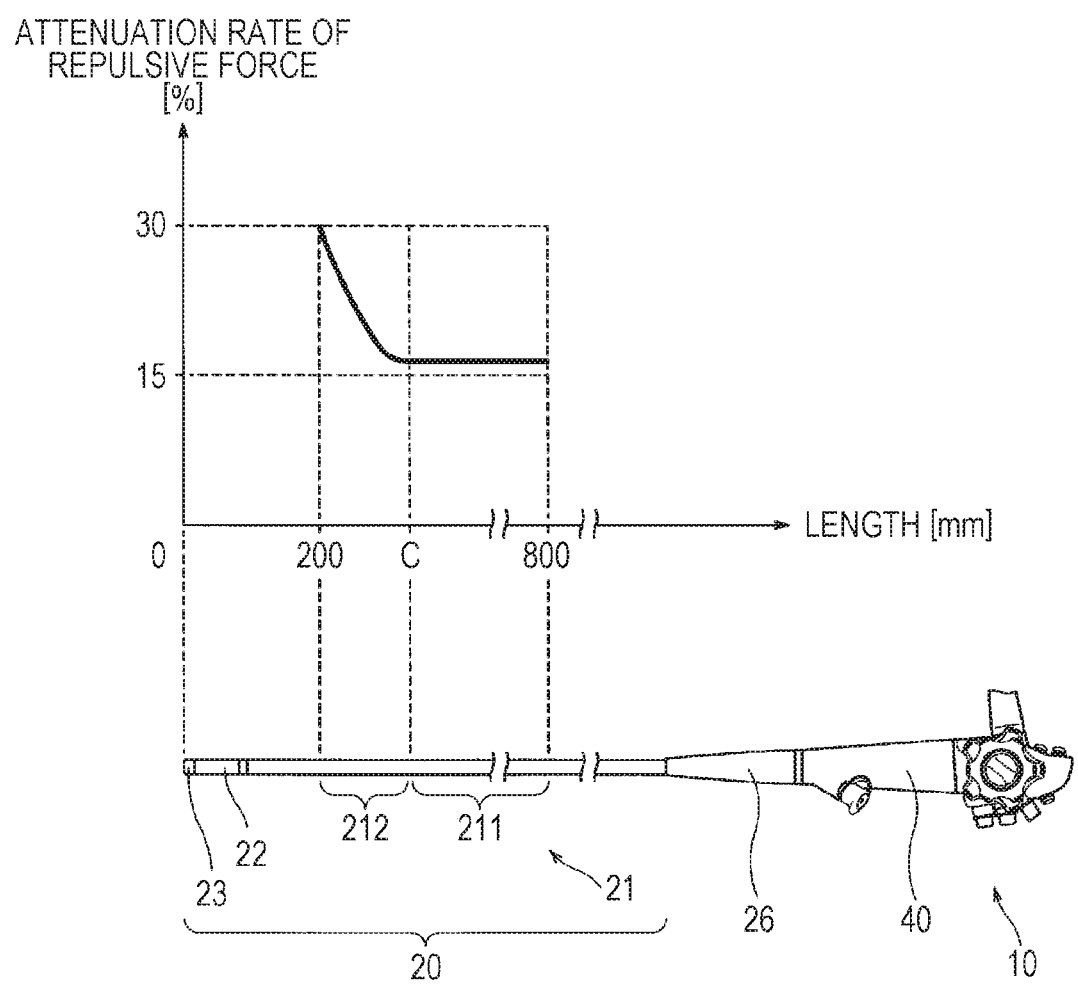
FIG. 8 is an explanatory view for describing an example of an attenuation rate of a repulsive force according to a second embodiment.

No. 8 is an explanatory view for describing an example of the attenuation rate of the repulsive force according to the second embodiment. An appearance of the endoscope 10 is illustrated on the lower side of FIG. 8. A graph of the repulsive force is illustrated on the upper side of FIG. 8. The horizontal axis of the graph represents a length from the distal end of the insertion unit 20, and the unit is a millimeter. A position on the horizontal axis corresponds to the appearance of the endoscope 10 illustrated on the lower side of FIG. 8.

The vertical axis of the graph represents the attenuation rate of the repulsive force of the soft portion. 21 described using FIGS. 1 to 6, and the unit is a percentage. In the present embodiment, the repulsive force and the attenuation rate thereof are not measured for a part whose horizontal axis is less than 200 mm. The attenuation rate of the repulsive force in a range of 200 mm or more and 800 mm or less on the horizontal axis is 30% or lower.

The attenuation rate of the repulsive force of a part in a range where the horizontal axis is longer than 800 mm is arbitrary, and may be 30% or lower or higher than 30%. Further, the attenuation rate of the repulsive force of this part may be uniform or may be changed along the insertion direction.

The soft portion 21 corresponding to a range of 200 mm to 800 mm on the horizontal axis will be described in more detail. The soft portion 21 includes the second area 212 corresponding to a range of 200 mm to C on the horizontal axis, and the first area 211 corresponding to a range of C to 800 mm on the horizontal axis. The second area 212 is adjacent to the distal end side of the first area 211.

C is 300 mm in the case of an endoscope for a lower gastrointestinal tract, and 500 mm in the case of an endoscope for an upper gastrointestinal tract.

In the second area 212, the attenuation rate of the repulsive force decreases in the form of an exponential function from the distal end side toward the first area 211. More specifically, the attenuation rate of the repulsive force monotonically decreases from the distal end side toward the first area 211. A decrease amount of the attenuation rate of the repulsive force per unit length, that is, the decrease rate of the attenuation rate of the repulsive force monotonically decreases from the distal end side toward the first area 211.

The attenuation rate of the repulsive force gradually decreases in the vicinity of a boundary between the second area 212 and the first area 211. In the first area 211, the attenuation rate of the repulsive force is substantially constant. The attenuation rate of the repulsive force in the first area 211 is, for example, 15% or higher.

The soft portion 21 of the present embodiment can be realized by, for example, changing a material of the hull 33, a thickness of the hull 33, a thickness of the top coat 34, a configuration of the reticular tube 32, or the like along the insertion direction.

When the hull 33 is a laminate of a plurality of resin layers, it is possible to realize the soft portion 21 of the present embodiment by changing a thickness ratio between the resin layers along the insertion direction. When the hull 33 is formed by mixing, a plurality of resin materials, it is possible to realize the soft portion 21 of the present embodiment by changing a mixing ratio of the resin materials along the insertion direction.

According to the present embodiment, the attenuation rate of the repulsive force is large at a part on the distal end side of the insertion unit 20, and this state is easily maintained when the insertion unit 20 is bent, and thus, it is possible to provide the endoscope 10 with a more favorable insertability.

Third Embodiment

The present embodiment relates to the endoscope 10 in which the second area 212 has a part where an attenuation rate of a repulsive force exceeds 30%. Descriptions regarding common parts with the second embodiment will be omitted.

Figure 9:
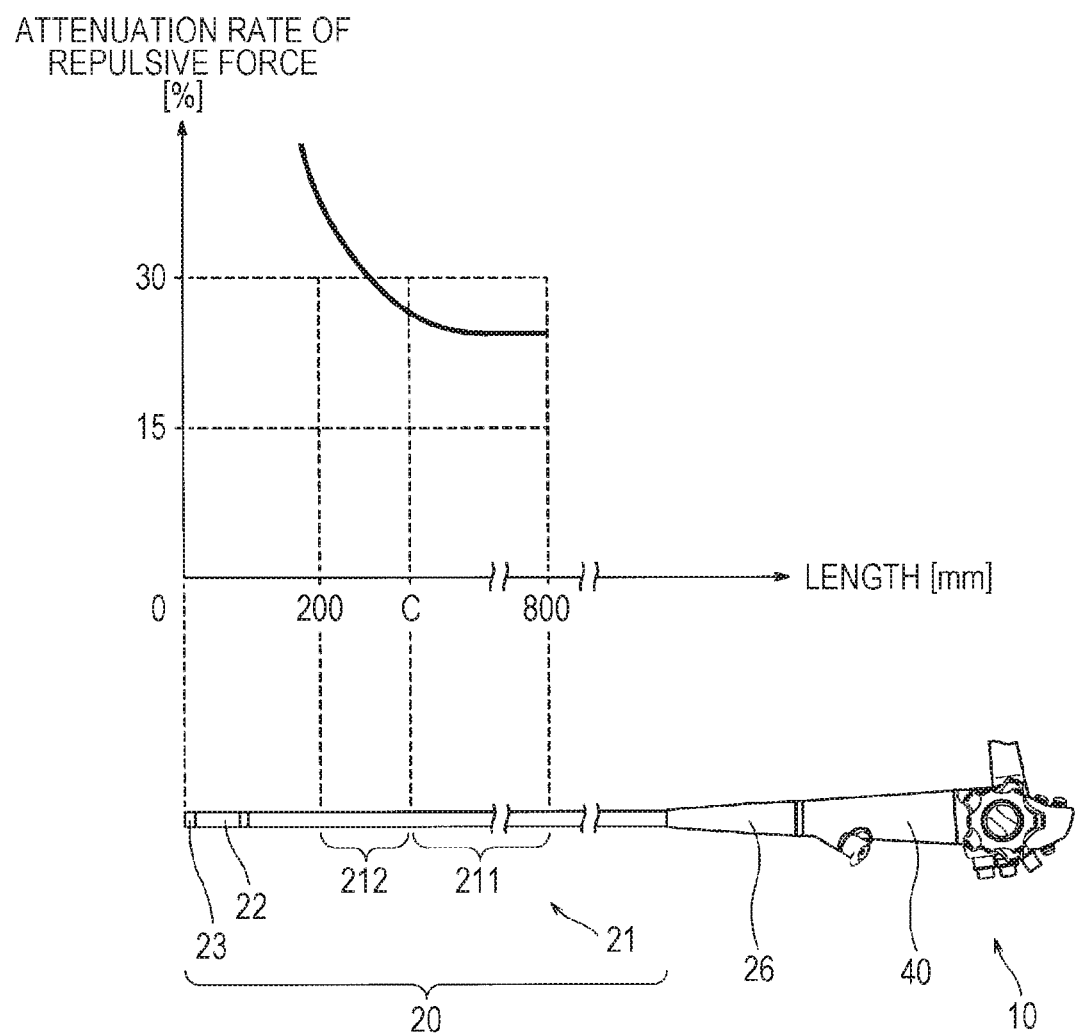
FIG. 9 is an explanatory view for describing an example of an attenuation rate of a repulsive force according to a third embodiment.

FIG. 9 is an explanatory view for describing an example of the attenuation rate of the repulsive force according to the third embodiment. An appearance of the endoscope 10 is illustrated on the lower side of FIG. 9. A graph of the repulsive force is illustrated on the upper side of FIG. 9. The horizontal axis of the graph represents a length from the distal end of the insertion unit 20, and the unit is a millimeter. A position on the horizontal axis corresponds to the appearance of the endoscope 10 illustrated on the lower side of FIG. 9.

The vertical axis of the graph represents the attenuation rate of the repulsive force of the soft portion 21 described using FIGS. 4 to 6, and the unit is a percentage. In the present embodiment, the repulsive force and the attenuation rate thereof are not measured for a part whose horizontal axis is less than 200 mm.

The attenuation rate of the repulsive force of a part in a range where the horizontal axis is longer than 800 mm is arbitrary, and may be 30% or lower or higher than 30%. Further, the attenuation rate of the repulsive force of this part may be uniform or may be changed along the insertion direction.

The soft portion 21 corresponding to a range of 200 mm to 800 mm on the horizontal axis will be described. The soft portion 21 includes the second area 212 corresponding to a range of 200 mm to C on the horizontal axis, and the first area 211 corresponding to a range of C to 800 mm on the horizontal axis. The second area 212 is adjacent to the distal end side of the first area 211.

C is 300 mm is the case of an endoscope for a lower gastrointestinal tract, and 500 mm in the case of an endoscope for an upper gastrointestinal tract.

In the second area 212, the attenuation rate of the repulsive force decreases in the form of an exponential function from the distal end side toward the first area 211. The attenuation rate of the repulsive force exceeds 30% on the distal end side of the second area 212, and the attenuation rate of the repulsive force is 30% or over on the first area 211 side of the second area 212.

The attenuation rate of the repulsive force gradually decreases in the vicinity of a boundary between the second area 212 and the first area 211. In the first area 211, the attenuation rate of the repulsive force is 30% or lower.

The soft portion 21 of the present embodiment can be realized by, for example, changing a material of the hull 33, a thickness of the hull 33, a thickness of the top coat 34, a configuration of the reticular tube 32, or the like along the insertion direction.

When the hull 33 is a laminate of a plurality of resin layers, it is possible to realize the soft portion 21 of the present embodiment by changing a thickness ratio between the resin layers along the insertion direction.

When the hull 33 is formed by mixing a plurality of resin materials, it is possible to realize the soft portion 21 of the present embodiment by changing a mixing ratio of the resin materials along the insertion direction.

According to the present embodiment, the attenuation rate of the repulsive force is large at a part on the distal end side of the insertion unit 20, and the similar behavior to the bending portion 22 is exhibited, and thus, it is possible to provide the endoscope 10 with a more favorable insertability.

Technical features (constitutional requirements) described in the respective embodiments can be combined with each other, and new technical features can be formed with the combination.

The embodiments disclosed herein are exemplary in all respects, and at should be considered that the embodiments are not restrictive. The scope of the present invention is defined not by the above-described meaning but by claims, and intends to include all modifications within meaning and a scope equal to claims.

Regarding the embodiments including the first to third embodiments, the following appendixes are additionally disclosed.

(Appendix 1)
An endoscope 10 including
an insertion unit 20 having a first area 211 in which an attenuation rate of a repulsive force generated when bent is a positive value of 30% or lower.

(Appendix 2)
The endoscope 10 according to Appendix 1, wherein
the attenuation rate of the first area 211 is 10% or higher and 30% or lower.

(Appendix 3)
The endoscope 10 according to Appendix 1 or 2, wherein
the first area 211 is in a range of 200 millimeters to 800 millimeters from a distal end side of the insertion unit 20.

(Appendix 4)
The endoscope 10 according to Appendix 1 or 2, wherein
the insertion unit 20 includes a second area 212 which is adjacent to a distal end side of the first area 211 and has a higher attenuation rate than an attenuation rate of the first area 211.

(Appendix 5)
The endoscope 10 according to Appendix 4, wherein the attenuation rate of the second area 212 is 30% or lower.

(Appendix 6)
The endoscope 10 according to Appendix 4 or 5, wherein the attenuation rate monotonously decreases from the distal end side toward the first area 211 in the second area 212.

(Appendix 7)
The endoscope as described in Appendix 6, wherein a decrease rate of the attenuation rate monotonously decreases from the distal end side toward the first area 211 in the second area 212.

(Appendix 8)
The endoscope 10 according to Appendix 4 or 5, wherein the attenuation rate exponentially decreases from the distal end side toward the first area 211 in the second area 212.

(Appendix 9)
The endoscope 10 according to any one of Appendixes 4 to 8, wherein
the second area 212 is in a range of 200 mm to 300 mm from the distal end side of the insertion unit 20, and
the first area 211 is in a range of 300 mm to 800 mm from the distal end side of the insertion unit 20.

(Appendix 10)

The endoscope 10 according to any one of Appendixes 4 to 8, wherein
the second area 212 is in a range of 200 mm to 500 mm from the distal end side of the insertion unit 20, and the first area 211 is in a range of 500 mm to 800 mm from the distal end side of the insertion unit.

(Appendix 11)

The endoscope 10 according to any one of Appendixes 1 to 10, wherein
the attenuation rate is calculated by Formula (1) based on a repulsive force A immediately after pushing the insertion unit 20 against a central point in a three-point bending tester with a spacing of 200 mm by 20 mm in a direction orthogonal to a length direction of the insertion unit 20 and a repulsive force B after a lapse of three seconds from a state of being pushed by 20 mm.

REFERENCE SIGNS LIST 10 endoscope
20 insertion unit
21 soft portion
211 first area
212 second area
22 bending portion
23 distal end portion
26 bend preventing portion
30 flexible tube
31 spiral tube
32 reticular tube
33 hull
34 top coat
40 operation unit
41 bending knob
42 channel inlet
43 forceps plug
50 connector unit
51 observation window
52 culmination window
53 air supply nozzle
54 water supply nozzle
55 channel outlet.
59 universal cord
70 measurement device
71 load measuring instrument
72 probe
73 pressing column.
74 auxiliary column

The invention claimed is:

1. An endoscope comprising
an endoscopic insertion unit affixed to an endoscopic operation unit, the endoscopic insertion unit having a first area and comprising:
a spiral tube comprising a spirally-wound metal strip;
a braided reticular tube surrounding the spiral tube;
a resin hull surrounding the braided reticular tube and comprising resin having a residual strain of 18% to 27%;
a resin outer coat surrounding the resin hull; and
a second area which is adjacent to a distal end side of the first area and has a higher attenuation rate than an attenuation rate of the first area, wherein
in the second area, the attenuation rate exponentially decreases from the distal end side toward the first area,
the first area is structured such that a repulsive force of the first area caused by bending the first area has an attenuation rate of a positive value equal to or less than 30 percent, the attenuation rate defined as a ratio between a repulsive force obtained immediately after bending the first area, and a repulsive force obtained after a state of bending the first area is maintained for three seconds, which is a period longer than a period of the repulsive force obtained immediately after bending, and
the attenuation rate is calculated by Formula (1) based on a repulsive force A immediately after pushing the insertion unit against a central point in a three-point bending tester with a spacing of 200 mm by 20 mm in a direction orthogonal to a length direction of the insertion unit and a repulsive force B after a lapse of three seconds from a state of being pushed by 20 mm:

[Formula 1]

$$C = \frac{A-B}{A} \times 100 \qquad (1)$$

A is a maximum value of a repulsive force,
B is a repulsive force after three seconds from push, and
C is an attenuation rate (percentage) of a repulsive force at a position of abutment on a probe.

2. The endoscope according to claim 1, wherein the attenuation rate of the first area is 10% or higher and 30% or lower.

3. The endoscope according to claim 1, wherein the first area is in a range of 200 mm to 800 mm from a distal end side of the insertion unit.

4. The endoscope according to claim 1, wherein the attenuation rate of the second area is 30% or lower.

5. The endoscope according to claim 1, wherein the attenuation rate monotonically decreases from the distal end side toward the first area in the second area.

6. The endoscope according to claim 5, wherein a decrease rate of the attenuation rate monotonically decreases from the distal end side toward the first area in the second area.

7. The endoscope according to claim 1, wherein the second area is in a range of 200 mm to 300 mm from the distal end side of the insertion unit, and the first area is in a range of 300 mm to 800 mm from the distal end side of the insertion unit.

8. The endoscope according to claim 1, wherein the second area is in a range of 200 mm to 500 mm from the distal end side of the insertion unit, and the first area is in a range of 500 mm to 800 mm from the distal end side of the insertion unit.

9. The endoscope according to claim 2, wherein the attenuation rate of the second area is 30% or lower.

10. The endoscope according to claim 2, wherein the attenuation rate monotonically decreases from the distal end side toward the first area in the second area.

11. The endoscope according to claim 2, wherein the second area is in a range of 200 mm to 300 mm from the distal end side of the insertion unit, and the first area is in a range of 300 mm to 800 mm from the distal end side of the insertion unit.

12. The endoscope according to claim 2, wherein the second area is in a range of 200 mm to 500 mm from the distal end side of the insertion unit, and the first area is in a range of 500 mm to 800 mm from the distal end side of the insertion unit.

13. The endoscope according to claim 5, wherein
the second area is in a range of 200 mm to 300 mm from the distal end side of the insertion unit, and
the first area is in a range of 300 mm to 800 mm from the distal end side of the insertion unit.

14. The endoscope according to claim 5, wherein
the second area is in a range of 200 mm to 500 mm from the distal end side of the insertion unit, and
the first area is in a range of 500 mm to 800 mm from the distal end side of the insertion unit.

* * * * *